United States Patent [19]

Siegall et al.

[11] Patent Number: 5,736,536
[45] Date of Patent: Apr. 7, 1998

[54] METHOD FOR TREATING VASCULAR LEAK SYNDROME

[75] Inventors: Clay Siegall; Dana Chace, both of Seattle, Wash.

[73] Assignee: Bristol-Myers Squibb Company, Princeton, N.J.

[21] Appl. No.: 795,751

[22] Filed: Feb. 6, 1997

Related U.S. Application Data

[62] Division of Ser. No. 293,351, Aug. 19, 1994.
[51] Int. Cl.⁶ .......................... A61K 31/60; A61K 61/54; A61K 31/54
[52] U.S. Cl. .................. 514/165; 514/226.5; 514/420; 514/568; 514/561; 514/570
[58] Field of Search .................. 514/226.5, 420, 514/568, 569, 570, 165

[56] References Cited

U.S. PATENT DOCUMENTS 5,278,143  1/1994  Shepro et al. .......................... 514/111

*Primary Examiner*—John W. Rollins
*Attorney, Agent, or Firm*—James M. Bogden; Joseph M. Sorrentino; Thomas R. Savitsky

[57] ABSTRACT

A novel method for preventing, stabilizing or causing regression of vascular leak syndrome is disclosed. The method comprises administering to a patient in need thereof a compound selected from the group consisting of a corticosteroid, a non-steroidal anti-inflammatory agent, 15-deoxyspergualin and related compounds, and phospholipase $A_2$ inhibitors.

9 Claims, 3 Drawing Sheets

METHOD FOR TREATING VASCULAR LEAK SYNDROME

This application is a divisional of application Ser. No. 08/293,351, filed Aug. 19, 1994, which application is incorporated herein in its entirety by reference.

BACKGROUND OF THE INVENTION

Vascular leak syndrome (VLS) is the dose-limiting toxicity found in many clinical trials utilizing immunotoxins, including those prepared with blocked ricin, ricin A chain (in native and deglycosylated forms), and saporin [Grossbard, M. L. et al., Blood 79, 576–585 (1992); Grossbard, M. L. et al., J. Clin. Oncol. 11, 726–737 (1993); Weiner, L. M. et al., Cancer Res. 49, 4062–4067 (1989); Vitetta, E. S. et al., Cancer Res. 51, 4052–4058 (1991); LeMaistre, C. F. et al., Blood 78, 1173–1182 (1991); Byers, V. S. et al., Blood 75, 1426–1432 (1990); Byers, V. S. et al., Cancer Res. 49, 6153–6160 (1989); Spitler, L. E. et al., Cancer Res. 47, 1717–1723 (1987); Amlot, P. L. et al., Blood 82, 2624–2633 (1993); Falini, B. et al., Lancet 339, 1195–1196 (1992)]. VLS is characterized in humans by hypoalbuminemia, weight gain, and edema, resulting from the extravasation of fluids and proteins from the vascular system into the periphery. VLS restricts the use of immunotoxins in humans and in many cases necessitates either a significant reduction in dose or a complete cessation of therapy. While peripheral edema is clinically manageable, pulmonary edema can be life threatening. Recently, VLS was found to have contributed to the death of two B-cell lymphoma patients who were treated with anti-CD22-deglycosylated ricin A chain [Amlot, P. L. et al., Blood 82, 2624–2633 (1993)]. Other toxic effects in patients treated with immunotoxins may be a result of VLS, including tachycardia, nausea, aphasias as a result of cerebral edema, and myocardial damage [Vitetta, E. S. et al., Cancer Res. 51, 4052–4058 (1991)].

Other proteins also have been found to induce VLS in humans. Systemic administration of the cytokine interleukin-2 (IL2) results in the development of VLS when approaching doses that may provide anti-tumor efficacy in patients with metastatic cancer [Rosenstein, M. et. al., Immunology 137, 1735–1742 (1986); Rosenberg, S. A. et al., N. Engl. J. Med. 316, 889–897 (1987)]. Patients treated with cumulative doses of 400 mg/m$^2$ of the anti-GD3 antibody R24 developed VLS within 24–36 hours of treatment [Bajourin, D. F. et al., Melanoma Res. 2, 355–362 (1992)]. VLS has also been observed in patients following treatment with granulocyte-macrophage colony-stimulating factor [Emminger, W. et al., Blut. 61, 219–221 (1990)]. It is apparent that the need exists for improved methods for treatment of VLS.

SUMMARY OF THE INVENTION

In accordance with the present invention, a novel method for preventing, stabilizing or causing the regression of VLS is disclosed. The method comprises the administration of a therapeutically effective amount of a compound selected from the group consisting of a corticosteroid, a non-steroidal anti-inflammatory agent, a phospholipase $A_2$ (PLA2) inhibitor, and 15-deoxyspergualin and related compounds to a mammalian species in need of such treatment.

As used in the present application, the term "vascular leak syndrome" means a syndrome characterized in humans by hypoalbuminemia, weight gain, and edema, resulting from the extravasation of fluids and proteins from the vascular system into the periphery.

The phrase "preventing" vascular leak syndrome as used in the present application refers to partially or fully inhibiting the development of VLS.

DESCRIPTION OF THE FIGURES

FIGS. 2A–2D. Histopathology of rat lungs (±Dex pretreatment) following BR96 sFv-PE40 administration. (A) Section from rat lung taken 24 hours following treatment (BR96 sFv-PE40 at 2 mg/kg), with pink peribronchovascular edema fluid (arrows) surrounding a pulmonary blood vessel. (B) Histologic section of rat lung taken from a rat pretreated with 1 mg/kg Dex for two days prior and on the same day as BR96 sFv-PE40 (2 mg/kg). The perivascular space is slightly widened by edema fluid demonstrating the ability of Dex pretreatment to eliminate or markedly reduce BR96 sFv-PE40-associated VLS. The thoracic cavity of this rat contained no free fluid. Magnification=75X.

DETAILED DESCRIPTION OF THE INVENTION

The methods of the present invention can be used for preventing, stabilizing or causing the regression of VLS. The vascular leak syndrome being treated can be caused in various ways. For example, VLS can be caused by bacterial infections, nitric oxide, viral infections and infections with helminthic parasites. It is preferred that the VLS result from administration of biological molecules, such as interferons (e.g., gamma interferon), cytokines and immunotoxins. For purposes of this application, a cytokine is defined as a protein factor than can cause proliferation and differentiation of blood cells. Examples of cytokines which induce VLS include interleukin-2 (IL-2), tumor necrosis factor alpha (TNF-α), and granulocyte-macrophage colony stimulating factor (GMCSF). For purposes of this application, an immunotoxin is defined as a chimeric molecule in which cell-binding ligands (or antibodies) are coupled to toxins, thus redirecting the cell-killing activity of the toxin to the receptor targeted by the cell binding moiety. Examples of immunotoxins include those prepared with blocked ricin, ricin A chain (in native and deglycosylated forms), PE40 and saporin [See., Grossbard, M. L. et al., Blood 79, 576–585 (1992); Grossbard, M. L. et al., J. Clin. Oncol. 11, 726–737 (1993); Weiner, L. M. et al., Cancer Res. 49, 4062–4067 (1989); Vitetta, E. S. et al., Cancer Res. 51, 4052–4058 (1991); LeMaistre, C. F. et al., Blood 78, 1173–1182 (1991); Byers, V. S. et al., Blood 75, 1426–1432 (1990); Byers, V.

S. et al., Cancer Res. 49, 6153–6160 (1989); Spitler, L. E. et al., Cancer Res. 47, 1717–1723 (1987); Amlot, P. L. et al., Blood 82, 2624–2633 (1993); Falini, B. et al., Lancet 339, 1195–1196 (1992)]. Specific immunotoxins include anti-Thy 1.2-ricin A chain [Vallera, D. A. et al., Blood 77, 182–194 (1991)], anti-GD3 antibody R24 [Bajorin, D. F. et al., Melanoma Res. 2, 355–362 (1992)], and BR96 sFv-PE40 [Friedman, P. N. et al., J. Immunol. 150, 3054–3061 (1993); Siegall, C. B. et al., J. Immunol. 152, 2377–2384 (1994)].

In accordance with the present invention, various materials can be used in treating VLS. Suitable materials include 15-deoxyspergualin (DSG) and related compounds. In particular, compounds of the following Formula A:

FORMULA A wherein Y is an alkylene group having an even number of from 4 to 10 carbons, preferably 6 or 8 carbons, or a meta or para mono- or dialkylenephenyl radical substituent group having in total 2 to 5 carbons in the alkylene residue(s), preferably 2 to 4 carbons, and X is an alkylene or aphahydroxyalkylene radical having 1 to 5 carbons, preferably 1 to 2 carbons, or an amino acid residue, especially Gly, L-His, L- and D-ser, γ-aba and DL-HABA, may be used. 15-Deoxyspergualin and a process for its preparation is described in U.S. Pat. No. 4,525,299 to Umezawa et al., while U.S. Pat. No. 4,851,446 to Umezawa, deceased, et al., describes an immunosuppressing method comprising the administration of 15-deoxyspergualin and related compounds. The No. '299 and No. '466 Umezawa patents are each incorporated herein by reference thereto.

Illustrative compounds of the structure (I) include those in which Y is $(CH_2)_6$ and X is CHOH, Y is $(CH_2)_6$ and X is Gly, Y is $(CH_2)_6$ and X is L-Ala, Y is $(CH_2)_6$ and X is L-Leu, Y is $(CH_2)_6$ and X is L-Phe, Y is $(CH_2)_6$ and X is L-Asp, Y is $(CH_2)_6$ and X is L-Gln, Y is $(CH_2)_6$ and X is L-Pro, Y is $(CH_2)_6$ and X is L-His, Y is $(CH_2)_6$ and X is L-Arg, Y is $(CH_2)_6$ and X is L-Ser, Y is $(CH_2)_6$ and X is D-Ser, Y is $(CH_2)_6$ and X is L-Thr, Y is $(CH_2)_6$ and X is β-ala, Y is $(CH_2)_6$ and X is γ-aba, Y is $(CH_2)_6$ and X is DL-HABA, Y is $pC_6H_4 (CH_2)_3$ and X is Gly, Y is $pC_6H_4 (CH_2)_3$ and X is L-Ser, Y is $p(CH_2)_3C_6H_4$ and X is Gly, Y is $p(CH_2)_3C_6H_4$ and X is Ser, Y is $pCH_2C_6H_4(CH_2)_2$ and X is Ser, Y is $mCH_2C_6H_4(CH_2)_2$ and X is Ser, Y is $pC_6H_4(CH_2)_4$ and X is Ser, Y is $pC_6H_4(CH_2)_5$ and X is Ser.

The deoxyspergualin compounds set forth above are typically used in the form of a pharmaceutically acceptable salt, for example, chloride and hydrochloride salts, especially the tri-hydrochloride salt.

15-Deoxyspergualin (DSG) has the structure (I) wherein Y is $(CH_2)_6$ and X is CHOH.

The clinically therapeutic dose of DSG and related compounds is from about 0.1 to about 40 mg/day/kg of patient body weight, and may be administered in single or divided doses in a systemic dosage form as described below for a period sufficient to prevent VLS. The peak plasma concentration obtained from such dose is from about 0.1 to about 20 µg/ml. Patients achieve a $C_{max}$ of approximately 10 µg/ml of DSG at 4 mg/kg by 3 hour i.v. infusion. Because of the relatively rapid clearance of DSG from plasma, this level drops quite rapidly. Thus, six hours following intravenous injection, the plasma concentration ranges from about 20 to 200 ng/ml. A delivery schedule resulting in a steady state plasma concentration of 10 to 200 ng/ml should therefore be effective for preventing VLS.

The present invention can also be practiced using DSG and related compounds as a racemic mixture, as well as the (+) and (−) isomers of DSG.

Other suitable materials include phospholipase $A_2$ ($PLA_2$) inhibitors. In particular, compounds which may be used are of the following Formula B:

FORMULA B wherein R=substituted or unsubstituted alkyl, arylalkyl, alkenyl or arylalkenyl groups having 6 or more carbon atoms; and X and Y are different and each is of the form wherein R' and R" are independently H or alkyl of $C_{1-6}$.

These compounds, their geometric isomers and their pharmaceutical salts may be used in preventing vascular leak syndrome.

The preparation and administration of the compounds of Formula B are described in U.S. Pat. No. 5,141,959, in U.S. patent application Ser. No. 079,072, filed on Jun. 16, 1993, abandoned, and in U.S. Pat. No. 5,436,369, which are incorporated herein by reference.

Particularly preferred are the compounds 11-cis, 13-cis-12 (3-carboxyphenyl) retinoic acid, having the formula:

and (2Z), (4Z)-3-methyl-4-(3-carboxyphenyl)-5-[1,2,3,4-tetrahydro-1,1,4,4-tetramethyl-6-anthracenyl]-2-4-pentadienoic acid, having the formula Additional suitable materials include corticosteroids such as dexamethasone, cortisone, hydrocortisone, prednisone, prednisolone, triamcinolone, methylprednisolone, betamethasone, flunisolide and beclomethasone dipropionate, and non-steroidal anti-inflammatory agents such as indomethacin, piroxicam, meclofenamate, naproxen, ibuprofen and aspirin. It is particularly preferred that the agent used to prevent VLS not affect the therapeutic activity of the agent causing VLS. For example, in the case of BR96 sFv-PE40, it is preferred that its anti-tumor activity not be abolished by the agent used to treat VLS.

In carrying out the methods of the present invention, the agent used to treat VLS may be administered to various mammalian species, such as monkeys, dogs, cats, rats, humans, etc., in need of such treatment.

The agent used to treat VLS may be administered systemically, such as orally or parenternally and may be administered intravenously, subcutaneously and intraperitoneally.

The agent used to treat VLS may be incorporated in a conventional dosage form, such as tablet, capsule, elixir or injectable. The above dosage forms will also include the necessary carrier material, exipient, lubricant, buffer, antibacterial, bulking agent (such as mannitol), anti-oxidants (ascorbic acid or sodium bisulfite) or the like. Oral dosage forms are preferred, although parenternal forms are quite satisfactory as well.

With regard to such systemic or local formulations, single or divided doses of from about 1 to 100 mg/kg, from 1 to 3 times daily, may be administered in systemic dosage forms as described above for a period sufficient to prevent VLS.

The exact route of administration, dosage form, mount to be administered and method of administration will vary depending on the agent employed and may readily be determined by one of ordinary skill in the art.

The following examples are further illustrative of the present invention. These examples are not intended to limit the scope of the present invention, and provide further understanding of the invention.

EXAMPLE I

I. MATERIALS AND METHODS

Reagents.

The single-chain immunotoxin fusion protein BR96 sFv-PE40 was expressed in *E. coli* and purified as previously described [Siegall, C. B., et al., J. Immunol 152, 2377–2384 (1994)]. Diphenhydramine-hydrochloride was purchased from Elkins-Sinn (Cherry Hill, N.J.). Cyclosporine A (CsA) was purchased from Sandoz (Basel, Switzerland). 15-Deoxyspergualin (DSG) was obtained from Nippon Kayaku (Tokyo, Japan). Dexamethasone (Dex) was purchased from Anpro Pharmaceuticals (Arcadia, Calif.).

Toxicity Studies

Six to eight week old female Wistar Furth and Rowett, nu/nu (athymic) rats (Harlan Sprague Dawley, Indianapolis, Ind.) were intravenously injected with various amounts of BR96 sFv-PE40 (0.25–4 mg/kg). After 24 hours, they were euthanized by exposure to $CO_2$, and the tissues analyzed using gross and microscopic techniques. Cardiac blood was collected from comatose animals and placed either in serum collection tubes for blood chemistry analysis or EDTA tubes for complete blood count (CBC). Hydrothorax fluid was collected from separate animals by placing the carcass in dorsal recumbancy, carefully removing the ventral chest wall and aspirating fluid using a 5 cc syringe and 21 g needle.

Histopathology of Rat Lungs Following Immunotoxin Therapy.

Trachea, lungs and heart were removed as a unit and the lungs were gently inflated with approximately 2 cc of fixative solution delivered via the trachea. These organs, as well as the chest wall, diaphragm, liver, kidney, and spleen were fixed for at least 48 hours in 10% neutral buffered formalin. Fixed tissues were processed for paraffin embedding, sectioned at 6 m and stained with hematoxylin and eosin for histologic evaluation.

Treatment Of Rats Carrying H3396 Tumor Xeno grafts. H3396 tumor xeno grafts were established in athymic rats as previously described [Siegall, C. B., et al., J. Immunol. 152, 2377–2384 (1994)]. Groups (n=6) were either left untreated, iv. injected with a single dose of BR96 sFv-PE40 (0.5 mg/kg), pretreated with three i.p. administrations of Dex (1 mg/kg) at 50, 26, and 2 hours prior to immunotoxin administration (0.5 mg/kg BR96 sFv-PE40), or pretreated with three i.p. injections of DSG (10 mg/kg) and immunotoxin as above.

II. RESULTS

Identification of Immunotoxin-Mediated Hydrothorax in Rats

Wistar Furth immunocompetent rats were intravenously administered with a single dose of BR96 sFv-PE40 (0.25 to 4.0 mg/kg). Necropsy was performed 24 hours following immunotoxin administration. The appearance of large amounts of clear fluid in the thoracic cavity (hydrothorax) was found to be dose dependent with doses of 2.0 mg/kg or greater resulting in fluid accumulations of >5 cc (Table 1). At 1 mg/kg, there was either small or no fluid accumulation and below 1 mg/kg, no fluid was detected. Acute toxicity was clinically apparent in rats treated at 2–4 mg/kg. Rats treated with 4 mg/kg BR96 sFv-PE40 (and not euthanized earlier) died within 72 hours. The cause of death in these rats was determined to be asphyxiation and other complications as a result of fluid accumulation in the lungs and thoracic cavity occurring within 48–72 hours after administration of BR96 sFv-PE40. Comparatively, doses of 0.25 and 0.5 mg/kg were previously used to promote tumor regressions without toxicity in xenografted rats [Siegall, C. B., et al., J. Immunol. 152, 2377–2384 (1994)].

Associated with an increase in thoracic fluid accumulation, there was a slight increase in hematocrit at 2 mg/kg and a dramatic increase at 3 and 4 mg/kg. There was also an opposing effect on serum albumin as decreased levels were found at 2 mg/kg or higher BR96 sFv-PE40 doses (Table 1). Hematocrit and serum albumin levels in the normal range were observed with BR96 sFv-PE40 doses of less than 2 mg/kg. Additionally, an increase in body weight (up to 10%) was associated with the onset of the hydrothorax in rats administered with BR96 sFv-PE40 at 1.5 mg/kg (maximum tolerated dose) within 7 days of administration (data not shown).

Histologic Evaluation

Figure 1A:
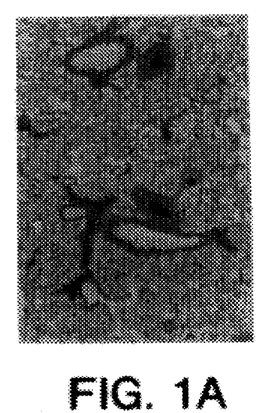
FIGS. 1A–1D. Histologic evaluation of BR96 sFv-PE40 treated rat lungs. (A) Lung section taken from an untreated rat. (B) Histologic section of lung taken from a rat treated 24 hours earlier with a single dose of BR96 sFv-PE40 at 2 mg/kg. The peribronchovascular spaces are markedly widened and contain pink edema fluid. (C) Scattered within the edema fluid are scant to moderate numbers of mixed inflammatory cells. (D) Representative alveolar section from the most severe expression of alveolitis, characterized by accumulation of alveolar macrophages mixed with fewer polymorphonuclear leukocytes, lymphocytes, and widely dispersed clumps of fibrin. Magnification: A and B=30X, C=150X, D=100X.
Figure 1B:
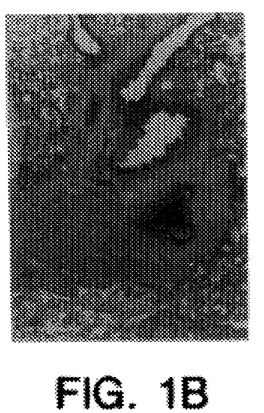
Figure 1C:
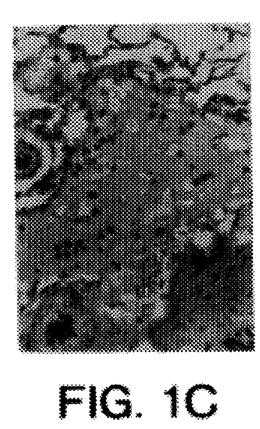
Figure 1D:
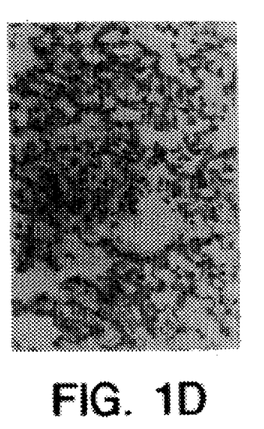

Histopathology was performed on rats sacrificed 24 hours after treatment with 2 mg/kg BR96 sFv-PE40 to assess tissue damage to major organs. Diffuse hepatocellular degeneration or less frequent, mild liver necrosis was occasionally observed. However, major histologic lesions were confined to the lungs of rats treated with immunotoxin. The principle histologic lesion was characterized by the accumulation of light pink fluid in the peribronchovascular space consistent with edema fluid (FIGS. 1A and B). The edema fluid filled lymphatics and dissected and expanded adjacent connective tissues. Alveolar walls were normal to very slightly thickened and there was scant to moderate pleural mesothelial cell hypertrophy. It was common for fluid accumulated in perivascular spaces to contain small numbers of mixed, but primarily mononuclear, inflammatory cells (FIG. 1C). In fewer than 25% of cases, lesions were slightly to moderately more severe with alveolar walls being prominently thickened and adjacent airspaces containing increased numbers of macrophages along with fewer polymorphonuclear leukocytes, lymphocytes, and erythrocytes (FIG. 1D).

Lack of VLS Symptoms in Mice

The hydrothorax found in rats following administration of 2–4 mg/kg BR96 sFv-PE40 was not seen in immunocompetent mice (Table 2). Serum albumin was constant and only a slight increase in hematocrit was observed at 2–4 mg/kg immunotoxin, doses that are lethal to mice. Severe hepatic lesions were found to be the dose-limiting toxicity in mice. Thus rats, but not mice, can serve as a model for BR96 sFv-PE40 induced VLS.

Assessment of Prophylactic Drug Treatment on Rats Prior to Immunotoxin Therapy

Utilizing this immunotoxin-induced rat VLS model, experiments were initiated to evaluate the effect of several anti-inflammatory and immunosuppressant drugs for ability to block hydrothorax. The drugs that were chosen were Diphenhydramine (anti-histamine), CsA (immunosuppressant), DSG (immunosuppressant), and Dex (anti-inflammatory/immunosuppressant). Rats were treated either with Diphenhydramine, 25 and 2 hours prior to immunotoxin administration, or CsA, DSG, or Dex, at 50, 26, and 2 hours prior to administration of BR96 sFv-PE40 (2 mg/kg). Dex pretreatment effectively blocked BR96 sFv-PE40-induced VLS in rats, with no detectable fluid accumulation in the thoracic cavity (Table 1 ). A variable though reproducible reduction in BR96 sFv-PE40-induced hydrothorax (0.5-5 cc) was observed in DSG pre-treated rats, while neither CsA nor Diphenhydramine were effective at blocking VLS (Table 1). These results show that Dex is a potent inhibitor of immunotoxin-induced VLS and DSG has a variable inhibitory effect on VLS.

Survival of Rats Administered With Lethal Doses of BR96 sFv-PE40

Since VLS is the dose limiting toxicity in BR96 sFv-PE40 treated rats, we evaluated the ability of these drugs to prevent immunotoxin-induced death. Rats were pretreated as described above, followed by administration of a lethal dose of BR96 sFv-PE40, 2 mg/kg, and were observed for survival until death or through day 10, post immunotoxin treatment. All rats treated with 2 mg/kg BR96 sFv-PE40 and no prophylaxis succumbed within 72 hours. All Dex pre-treated rats survived the otherwise lethal dose of immunotoxin (Table 3). No evidence of hydrothorax or other gross lesions were detected at necropsy. Neither CsA nor Diphenhydramine prophylaxis resulted in prolongation of survival. Injection of rats with Dex either at the same time or 24 hours following BR96 sFv-PE40 administration was unable to prevent hydrothorax or prolong survival. Thus, exposure to Dex, prior to immunotoxin administration, is necessary for the prevention of hydrothorax.

Effects of BR96 sFv-PE40 and VLS-Blocking Drugs on Blood Chemistry and CBC in Rats VLS induced by immunotoxins has been shown to be associated with hematologic changes. Since Dex, and to a lesser extent DSG, were found to block VLS in BR96 sFv-PE40 treated rats, we investigated the effects of these drug combinations on immunotoxin-induced changes in rat blood chemistry and CBC. BR96 sFv-PE40 (2 mg/kg) administration caused an increase in polymorphonuclear cells and hematocrit in peripheral blood, while decreasing the monocyte count (Table 4). Total white blood cell counts were within normal limits. Pre-treatment with Dex, followed by BR96 sFv-PE40 resulted in a leukocytosis and neutrophilia along with a rise in hematocrit, both predictable side-effects of Dex [Duncan. J. R. and Prasse, K. W., *Veterinary Laboratory Medicine,* 2nd ed., Iowa State Univ. Press, Ames, Iowa, 124–126 (1986); Haynes, R. C. and Murad, F., *The Pharmacological Basis of Therapeutics,* 7th ed., (MacMillan Pub. Co., N.Y., 1459–1489 (1985)]. As expected, the lymphocyte count was depressed in these rats. DSG pre-treatment had a minor suppressive effect on all immunotoxin-induced hematologic changes, and ameliorated the elevated hematocrit induced by BR96 sFv-PE40 (Table 4). However, DSG caused a pronounced decrease in monocytes consistent with the general myelosuppression effect of DSG that had been previously reported [Nemoto, K. et al., Jpn. J. Cancer Res. 83, 789–793 (1992)].

The effects of various treatments on blood chemistry was also compared at 2 mg/kg BR96 sFv-PE40. BR96 sFv-PE40 induced a mild increase in the liver enzymes serum glutamic-pyruvic transaminase (SGPT) and serum glutamic-oxaloacetic transaminase (SGOT) by 6 and 3-fold, respectively, as well as a decrease in both albumin and total protein (Table 4). Rats pre-treated with Dex followed by BR96 sFv-PE40 were found to have extremely elevated SGPT and SGOT levels (36–50 fold) as well as slightly elevated albumin and total protein levels, all of which are secondary to Dex treatment. Rats treated with Dex only had slightly elevated transaminases (71 and 153, for SGPT and SGOT, respectively). Thus, Dex appears to exacerbate the hepatotoxicity of BR96 sFv-PE40 by increasing the transaminase levels.

Histologic Examination of Dex Pretreated Lungs

Figure 2A:
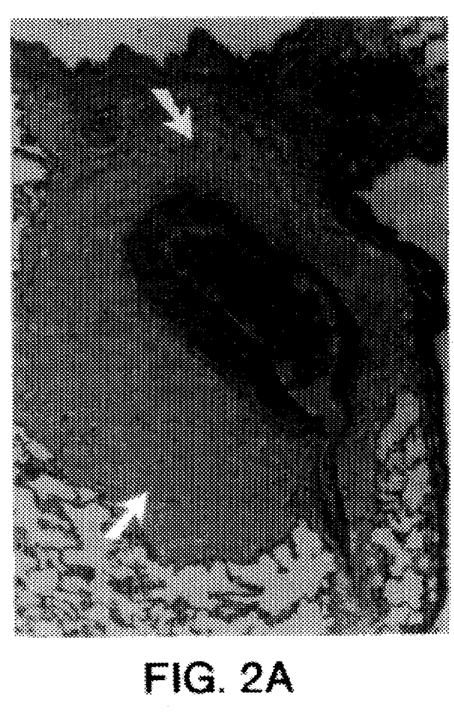
Figure 2B:
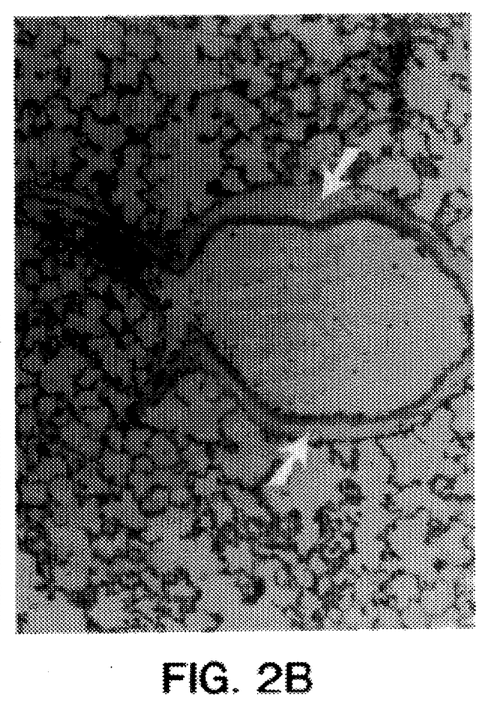

The effects of Dex pretreatment on rats receiving 2 mg/kg BR96 sFv-PE40 was evaluated histologically 24 hours after immunotoxin administration. Animals pretreated with Dex had only slight vascular edema or were indistinguishable from the control animals receiving no immunotoxin, whereas unprotected rats exhibited marked accumulation of fluid in the perivascular and surrounding parenchymal spaces (FIG. 2). Thus, pretreatment of rats receiving 2 mg/kg BR96 sFv-PE40 and 1 mg/kg Dex blocks both gross and microscopic evidence of pulmonary edema.

Figure 3:
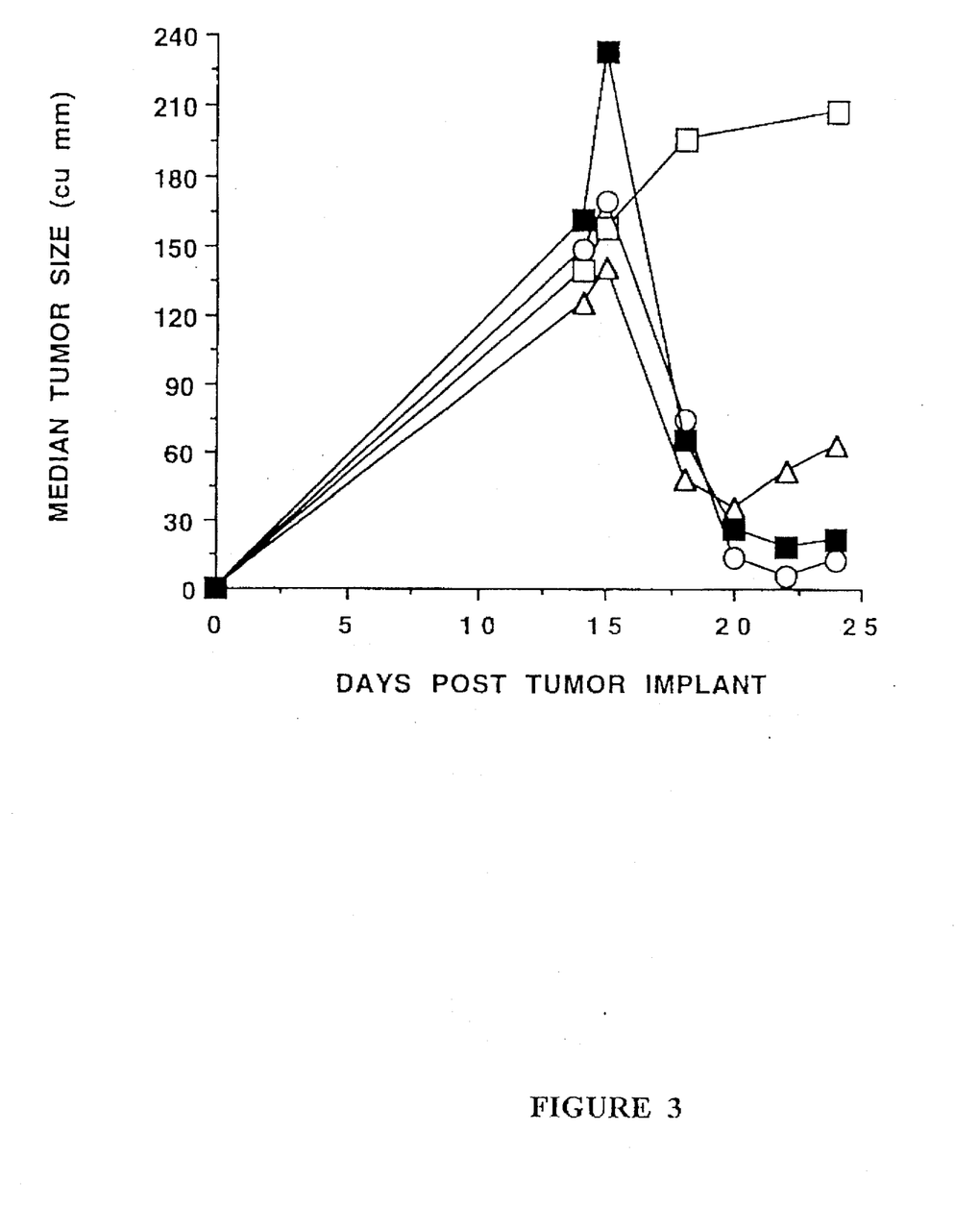
FIG. 3. Effect of Dex or DSG on BR96 sFv-PE40 Antitumor Activity in Rats Xenografted with H3396 Human Breast Carcinoma. BR96 sFv-PE40, 0.5 mg/kg (2.95 mg/m$^2$), (O); Dex, 1 mg/kg protreatment, BR96 sFv-PE40, 0.5 mg/kg, (2.95 mg/m$^2$), (△); DSG, 10 mg/kg pretreatment, BR96 sFv-PE40, 0.5 mg/kg, (2.95 mg/m$^2$), (■); non-treated control, (□).

Dex or DSG Does Not Abrogate the Antitumor Activity of BR96-Immunotoxin on Tumor Xenografts in Rats Dex and DSG are both immunomodulating agents. Having determined that Dex and to a lesser extent DSG, inhibits VLS in BR96 sFv-PE40 (2 mg/kg) treated rats, we next evaluated whether or not they would interfere with immunotoxin activity against tumors in vivo. The antitumor activity of BR96 sFv-PE40 has previously been measured against H3396 human breast carcinoma xenografts in rats [Siegall, C. B. et al., J. Immunol. 152, 2377–2384 (1994)]. Since the rats used in the antitumor study were athymic, we also tested the ability of athymic rats to develop dose-dependent hydrothorax. The same accumulation of thoracic fluid was found in the athymic rats as was found in the immunocompetent rats. Using the H3396 model, rats were pretreated with either Dex or DSG, followed by a single suboptimal intravenous dose of BR96 sFv-PE40 (0.5 mg/kg). Regressions of the H3396 tumor xenografts were observed in the immunotoxin treated animals, with or without Dex or DSG pre-treatment (FIG. 3). In the Dex pre-treated group, there was a slight reduction in the regression of the tumor xenograft in comparison with tumors in both the DSG or non-pretreated groups. Thus, pre-treatment of rats with the immunomodulatory agents Dex or DSG does not block BR96 sFv-PE40 from regressing implanted tumor xenografts.

III. DISCUSSION

Immunotoxin therapy is a promising approach for the treatment of cancer [Grossbard, M. L. and Nadler, L. M., *Important Advances in Oncology,* (J. P. Lippincott Co., Philadelphia, Pa.), 111–135 (1992); Pasten, I. et al., Annu. Rev. Biochem. 61, 331–354 (1992)]. However, dose-limiting side-effects have prevented the use of sufficient amounts needed for the best therapeutic response. VLS has been the most limiting of these side-effects [Vitetta, E. S. et al., Cancer Res. 51, 4052–4058 (1991); Vitetta, E. S. et al., Trends Pharm. Sci. 14, 148–154 (1993)]. For immunotoxins to become effective drugs for the treatment of human cancer, prevention of immunotoxin-induced VLS is necessary. Studies in non-human primates suggest that these models may be poor predictors of VLS toxicity in humans, as evidenced by the lack of VLS in monkeys and presence of VLS in humans treated with B3-LysPE40 immunoconjugates [Pai, L. H. et al., Cancer Res. 52, 3189–3193 (1992); Skolnick, A. A., JAMA 270, 2280 (1993)]. No immunocompetent animal model of immunotoxin-induced VLS has been described to date. Administration of ricin A chain-immunotoxins was reported to be unable to induce VLS in immunocompetent mice, rats, or guinea pigs [Soler-Rodrigues, A. M. et al., Exp. Cell. Res. 206, 227–234 (1993)]. However, it has been reported that irradiated mice displayed VLS symptoms following administration of the pan T-cell immunotoxin anti-Thy 1.2-ricin A chain [Vallera, D. A. et al., Blood 77, 182–194 (1991)].

In vitro experimentation to investigate VLS has been performed because of the lack of an adequate in vivo model. It has been demonstrated that ricin A chain could be directly cytotoxic to endothelial cells [Soler-Rodrigues, A. M. et al., Exp. Cell. Res. 206, 227–234 (1993)]. However, it is not clear whether or not in vivo toxicity to endothelial cells is, in fact, the cause of immunotoxin-induced VLS.

We have focused on establishing an animal model that approximates VLS as seen in human clinical trials utilizing targeted immunotoxins. Rats administered with the single-chain immunotoxin BR96 sFv-PE40 responded with a dose-dependent VLS similar to that seen in humans. The VLS response was seen as an accumulation of thoracic fluid and pulmonary edema with a concomitant increase in hematocrit and body weight as well as a decrease in serum albumin levels (Table 1). The rats died within 48–72 hours after administration of BR96 sFv-PE40 as a result of fluid accumulation in the lungs and thoracic cavity.

In contrast, there were no VLS symptoms in mice administered with BR96 sFv-PE40 at doses up to 4 mg/kg, in which mice died due to hepatic toxicity (Table 2). Preliminary studies indicate that dogs do not respond to BR96 sFv-PE40 with any VLS-like symptoms at doses at least 6-times higher (on a mg/m$^2$ basis) than that causing a VLS response in a rat (data not shown). Additionally, there were no apparent VLS symptoms in monkeys following administration of immunotoxins prepared with both ricin A chain and PE40 [Vitetta, E. S. et al., Cancer Res. 51, 4052–4058 (1991); Pai, L. H. et al., Cancer Res. 52, 3189–3193 (1992)]. Thus, rats represent the only species described so far to naturally respond to an immunotoxin like that seen in humans.

To accurately evaluate the toxicity of immunotoxins, standard screening of more than two species (often done with mouse and monkey) may be necessary. While rats provide a useful model for BR96 sFv-PE40-induced toxicity because they respond with a dose-limiting VLS, they may not be the optimal species for other immunotoxins with different specificities or with different toxins. Therefore, continued experimentation in evaluating the toxicity of other immunotoxins in the rat model, specifically focusing on VLS symptoms, has been initiated.

Having a model for Le$^y$-immunotoxin-induced VLS, we set out to search for inhibitors of VLS that could be combined with the immunotoxin without masking its antitumor activity. Of the drugs tested, Dex totally blocked, and DSG variably inhibited immunotoxin-induced VLS (Table 3). Additionally, Dex prevented death in rats treated with an otherwise lethal dose (2 mg/kg) of BR96 sFv-PE40 (Table 3), while DSG did not. However, Dex was unable to prolong survival in rats treated with 4 mg/kg BR96 sFv-PE40 (data not shown). The mechanism whereby Dex suppresses VLS in this model system is unclear. Glucocorticoids are capable of exerting a multiplicity of antiinflammatory and immunosuppressive effects including blockade of arachidonate metabolism, suppression of lymphocyte and macrophage functions with marked lympholysis in rodents, down-regulation of several pro-inflammatory cytokines, and stabilization of mast cells among others [Haynes, R. C. and Murad, F., *The Pharmacological Basis of Therapeutics*, (MacMillan Pub. Co., N.Y.), 1459–1489 (1985); Boumpas, D. T. et al., Clin. Exp. Rheum. 9, 413–423 (1991)]. The absence of any modulating effects following CsA pre-treatment and the presence of an effect in athymic rats suggest that in this model, VLS is not mediated by classic T-cell responses. The variable regulation of VLS associated with DSG pre-treatment, along with the potent effect of Dex suggests that the targets influenced by these immunosuppressive drugs may be critical to the pathogenesis of VLS in rats.

While VLS is the dose-limiting toxicity of many immunotoxins, it remained to be determined whether the same properties that mediate VLS are also responsible for tumor reduction. To address this issue, the effects of Dex or DSG prophylaxis on immunotoxin anti-tumor activity was studied in athymic rats carrying established H3396 human breast carcinomas. It was found that tumor xenografts in rats pretreated with either drug underwent regression similarly as compared to xenografts in rats treated with BR96 sFv-PE40 alone (FIG. 3), although xenografts in rats that received prophylactic Dex were regressed slightly less compared to xenografts in non-pretreated rats or those pretreated with DSG. One explanation for the slight reduction in antitumor activity is that Dex has been shown to decrease the delivery of a carcinoma reactive monoclonal antibody to tumor xenografts in athymic rats [Neuwelt, E. A. et al., Neurosurgery 33, 478–484 (1993)]. Thus, in our study, the immunotoxin may have been slightly retarded from leaving the vasculature in Dex treated animals. However, since we specifically used a suboptimal treatment of immunotoxin and could only detect a slight difference between Dex pre-treated and control groups, while the same level of Dex completely prevented all signs of VLS, it suggests that at least in the rat model, antitumor activity and VLS occur by separate mechanisms.

DSG is currently undergoing clinical evaluation for suppression of HAMA in cancer patients treated with an antibody or antibody-based imaging agent. Preliminary results from these studies suggest that DSG is effective at blocking HAMA. These results combined with our results showing DSG inhibits VLS in rats without abolishing antitumor effects of BR96 sFv-PE40, support the further investigation of DSG in the clinic for combination therapy with immunotoxins.

IL-2 has also been found to cause VLS in humans [Rosenstein, M. et. al., Immunology 137, 1735–1742 (1986); Rosenberg, S. A. et al., N. Engl. J. Med. 316, 889–897 (1987)]. Corticosteroids have been shown to reduce IL-2 mediated side effects [Vetto, J. et al., J. Clin. Oncol. 5, 496–503 (1987); Mier, J. W. et al., Blood 76, 1933–1940 (1990)]. However, corticosteroids also reduce the antitumor effect of IL-2 in mouse models of cancer since they are immunosuppressive and inhibit adoptive immunotherapy [Papa, M. Z. et al., Cancer Res. 46, 5618–5623 (1986)]. Corticosteroids have been administered either concurrently or subsequent to use of anti-CD22-ricin A chain immunotoxin conjugates in humans, based on the ability of corticosteroids to inhibit IL-2 induced VLS [Vitetta, E. S. et al., Cancer Res. 51, 4052–4058 (1991); Amlot, P. L. et al., Blood 82, 2624–2633 (1993)]. These limited studies were unable to correlate the grade of toxicity in groups of patients that received corticosteroids in combination with immunotoxin, nor were they able to determine whether corticosteroids masked the ability of immunotoxins to regress tumors. Pentoxifylline, a synthetic xanthine, has been shown to inhibit IL-2 induced VLS in rats [Edwards, M. J. et al., Surgery 110, 199–204 (1991); Edwards, M. J. et al., J. Clin. Invest. 90, 637–641 (1992)], and guinea pigs [Ishizaka, A. et al., J. Appl. Physiol. 67, 2432–2437 (1989)], and tumor necrosis factor-alpha (TNF-α) induced VLS in guinea pigs [Lilly, C. et al., Am. Rev. Respir. Dis. 139: 1361–1368 (1989)]. Our data suggests that prophylactic treatment may be the key to blocking VLS induced by immunotoxin therapy.

EXAMPLE 2

Additional drugs were screened for their ability to prevent BR96 sFv-PE40-mediated VLS in rats (Table 5). Prophylactic administration of indomethacin, a non-steroidal anti-inflammatory drug (NSAID), prevented hydrothorax in rats treated with 2 mg/kg BR96 sFv-PE40. However, the dose range of indomethacin that was effective in preventing VLS (15–30 mg/kg) was higher than usually used clinically. At 5 mg/kg, indomethacin was unable to prevent BR96 sFv-PE40-mediated VLS. Piroxicam, also an NSAID, was found to prevent VLS in the same model system when administered prophylactically either i.p. or orally with a dose of 20 mg/kg.

The PLA$_2$ inhibitor 11-cis, 13-cis-12 (3-carboxyphenyl) retinoic acid was also found to prevent VLS in rates following administration of BR96 sFv-PE40. With prophylactic administration (i.p.) of 11-cis, 13-cis-12 (3-carboxyphenyl) retinoic acid, VLS was reduced by 50% (30 mg/kg) or completely blocked (100 mg/kg).

Indomethacin, as well as other NSAIDs, act by blocking the enzyme cyclooxygenase, thus preventing the generation of prostaglandin endoperoxides (from which prostaglandins and thromboxanes are metabolized) from arachidonic acid. The PLA$_2$ inhibitor 11-cis, 13-cis-12 (3-carboxyphenyl) retinoic acid blocks the generation of arachidonic acid from membrane phospholipids. These date are suggestive of a major role for prostanoids and specifically prostaglandins in the advent of BR96 sFv-PE40 mediated VLS.

TABLE 1

Identification of an Immunotoxin-Mediated, Dose-Dependent Hydrothorax Condition in Rats

| IT Dose, mg/kg (mg/m$^2$) | Hydrothorax (cc) | Hematocrit (%) | Albumin (g/dl) |
|---|---|---|---|
| 0 | 0 | 38.9 | 3.6 |
| 0.25 (1.475) | 0 | 39.9 | 3.8 |
| 0.5 (2.95) | 0 | 39.7 | 3.5 |
| 1.0 (5.9) | 0–3* | 39.5 | 3.2 |
| 2.0 (11.8) | >5 | 42.9 | 2.6 |
| 3.0 (17.7) | >5 | 56.1 | 2.5 |
| 4.0 (23.6) | >5 | 55.5 | 2.6 |

TABLE 1-continued

Identification of an Immunotoxin-Mediated, Dose-Dependent Hydrothorax Condition in Rats

| IT Dose, mg/kg (mg/m$^2$) | Hydrothorax (cc) | Hematocrit (%) | Albumin (g/dl) |
|---|---|---|---|

BR96 sFv-PE40 was intravenously administered in a volume of 0.2 ml in PBS. Fluid accumulation into the thoracic cavity was collected 24 hours after administration of IT (2–4 animals were treated at each dose). Five cc of hydrothorax fluid indicates a range between 5–8 cc.
*2/3 rat had no fluid and 1/3 had 3 cc hydrothorax fluid.

TABLE 2

LACK OF HYDROTHORAX IN MICE

| IT Dose, mg/kg (mg/m$^2$) | Hydrothorax (cc) | Hematocrit (%) | Albumin (g/dl) |
|---|---|---|---|
| 0 | 0 | 36.4 | 3.15 |
| 2.0 (6.0) | 0 | 42.8 | 3.3 |
| 4.0 (12.0) | 0 | 46.0 | 3.3 |

BR96 sFv-PE40 was administered and fluid accumulation measure as in Legend for Table 1.

TABLE 3

PREVENTION OF VLS

| IT Dose (mg/kg) | Pretreatment | Hydrothorax (cc) (24 h) | Survival at 10 d (# alive/# total) |
|---|---|---|---|
| 2 | Dexamethasone | 0 | 10/10 |
| 2 | Deoxyspergualin | 0.5–5.0 | 0/5 |
| 2 | Cyclosporine A | >5 | 0/3 |
| 2 | None | >5 | 0/10 |
| 2 | Diphenylhydramine | >5 | 0/3 |

BR96 sFv-PE40 was administered intravenously in 0.2 ml PBS either alone or two hours following the last pretreatment dose of dexamethasone (1 mg/kg, q1dx3, intraperitoneal); deoxyspergualin (10 mg/kg, q1dx3, intraperitoneal); cyclosporine A (100 mg/kg, q1dx3, subcutaneous), diphenylhydramine (1 mg/kg, q1 dx2, intraperitoneal). IT = immunotoxin (BR96 sFv-PE40).

TABLE 4

CBC AND CHEMISTRY SCREEN CHART

| Cell Type | Untreated | IT only | Dexamethasone + IT | Deoxyspergualin + IT |
|---|---|---|---|---|
| WBC | 13.0 | 13.8 | 16.9 | 9.2 |
| Poly | 1593 | 5032 | 13130 | 328 |
| Lymph | 8217 | 7322 | 2584 | 5587 |
| Mono | 659 | 395 | 486 | 230 |
| Hemato. | 36.8 | 48.6 | 53.1 | 38.9 |
| CHEMISTRY SCREEN | | | | |
| SGPT | 56 | 301 | 5790 | 113 |
| SGOT | 99 | 299 | 3641 | 131 |
| Albumin | 3.6 | 2.8 | 4.5 | 3.2 |
| Tot. Prot | 6.7 | 5.0 | 7.1 | 6.3 |

Data (average of 2–4 rats) are taken 24 hours post-IT administration (2 mg/kg). WBC count in thousands/mm$^3$; polymorphonuclear cells, lymphocytes and monocytes are in absolute numbers; Hematocrit is in %, SGPT and SGOT are in iu/l, albumin and total protein are in g/dl.

TABLE 5

VLS INHIBITOR STUDY

| # Rats | Pretreatment | Treatment | Hydrothorax (cc) |
|---|---|---|---|
| 4 | Indomethacin; 30 mg/kg, sc | BR96 sFv-PE40, 2 mg/kg, iv | 0 |
| 2 | Indomethacin; 15 mg/kg, sc | Same | 0 |
| 2 | Indomethacin; 5 mg/kg, sc | Same | >5 |
| 2 | 11-cis, 13-cis-12 (3-carboxyphenyl) retinoic acid; 30 mg/kg, ip | Same | 2.5 |
| 2 | 11-cis, 13-cis-12 (3-carboxyphenyl) retinoic acid; 100 mg/kg, ip | Same | 0 |

What is claimed:

1. A method for preventing vascular leak syndrome comprising administering to a mammalian species in need thereof a therapeutically effective amount of a non-steroidal antiinflammatory agent selected from the group consisting of indomethacin, piroxicam, meclofenanate, naproxen, ibuprofen and aspirin.

2. The method according to claim 1, wherein the non-steroidal anti-inflammatory agent is indomethacin.

3. The method according to claim 1 wherein the non-steroidal anti-inflammatory agent is piroxicam.

4. The method according claim 1 wherein the vascular leak syndrome is caused by a biological molecule.

5. The method according to claim 4 wherein the biological molecule is a cytokine.

6. The method according to claim 4 wherein the biological molecule is an interferon.

7. The method according to claim 4 wherein the biological molecule is an immunotoxin.

8. The method according to claim 7 wherein the immunotoxin is BR96 sFv-PE40.

9. The method according to claim 1 wherein the mammalian species is a human.

* * * * *